United States Patent [19]

Schwartz et al.

[11] Patent Number: 5,304,122
[45] Date of Patent: Apr. 19, 1994

[54] METHOD FOR PROVIDING A RESTENOSIS MODEL IN PORCINE CORONARY ARTERIES

[75] Inventors: Robert S. Schwartz; Joseph G. Murphy, both of Rochester; Rodney G. Wolff, Minnetonka Beach; Vincent W. Hull, Ham Lake, all of Minn.

[73] Assignee: Medtronic, Inc., Minneapolis, Minn.

[21] Appl. No.: 981,959

[22] Filed: Nov. 24, 1992

Related U.S. Application Data

[63] Continuation-in-part of Ser. No. 655,912, Feb. 14, 1991, abandoned.

[51] Int. Cl.$^5$ ............................................. A61M 31/00
[52] U.S. Cl. ................................... 604/53; 128/898; 606/195
[58] Field of Search .................... 604/49, 52, 53, 96; 606/108, 153, 191, 194, 195, 198; 623/1, 11; 128/898

[56] References Cited

U.S. PATENT DOCUMENTS 4,886,062  12/1992  Witkor .................................. 623/1

OTHER PUBLICATIONS

Schwartz, A Practical Porcine Model of Human Coronary Artery Restenosis Post PTCA, Abstract, JACC vol. 15, No. 2, Feb. 1990: 165A.
"A Cascade Model for Restenosis. A Special Case of Atherosclerosis Progression", by P. Libby et al., Circulation 86(6) III-47-52, Dec., 1992.
"Restenosis After Balloon Angioplasty-A Practical Proliferative Model in Porcine Coronary Arteries", by Robert S. Schwartz et al., Circulation, 82(6):2190-2200, Dec., 1990.
"Restenosis and the Proportional Neointimal Response to Coronary Artery Injury: Results in a Porcine Model" by Robert S. Schwartz, et al., J. Am. Coll. Cardiol; 19; 267-274, Feb., 1992.
"The Restenosis Paradigm Revisted: An Alternative Proposal for Cellular Mechanisms" [editorial], Robert S. Schwartz et al., J. Am. Coll. Cardiol; 20(5) 1284-1293, Nov., 1992.

Primary Examiner—John D. Yasko
Assistant Examiner—Anthony Gutowski
Attorney, Agent, or Firm—Daniel W. Latham; Harold R. Patton

[57] ABSTRACT

A model of arterial restenosis in domestic pigs using deep injury to the coronary arterial media resulting in extensive proliferative response. Metal wire coils are delivered percutaneously to the coronary arteries of pigs with an oversized, high pressure (14 atm) balloon and left in place for 5-6 weeks. During placement, the balloon expands the coils and delivers them securely within the arterial lumen causing fracture of the internal elastic lamina by the coil. An extensive proliferative response occurs and is associated with a lumenal area narrowing of at least 50% Immunohistochemical studies confirms the prominence of smooth muscle cells in the tissue. The histopathologic features of the proliferative response are identical to those observed in cases of restenosis post-angioplasty.

This model closely mimics the proliferative portion of human restenosis both grossly and microscopically. It may thus be useful for understanding human restenosis and for testing therapies aimed at preventing restenosis after balloon angioplasty or other coronary interventional procedures.

5 Claims, 10 Drawing Sheets

METHOD FOR PROVIDING A RESTENOSIS MODEL IN PORCINE CORONARY ARTERIES

This is a continuation-in-part of copending application Ser. No. 07/655,912 filed on Feb. 14, 1991 (now abandoned).

BACKGROUND OF THE INVENTION

1. Field of the Invention

This invention relates to a method for inducing arterial restenosis in an animal model in order to study potential therapies for application to restenosis occurring in human patients after balloon angioplasty or other coronary interventional procedures.

2. Description of the Prior Art

Blood vessels narrowed or occluded by disease have been surgically repaired or replaced in bypass procedures for many years. More recently, percutaneous transluminal coronary angioplasty (PTCA) and intraluminal endovascular grafting procedures employing PCTA balloons and expandable stents have been developed and widely employed to avoid the expense and trauma of vascular surgery.

Despite the high initial success rate and widespread use of percutaneous transluminal coronary angioplasty (PTCA), restenosis appreciably limits the effectiveness of this valuable revascularization method. (See K. M. Kent, "Restenosis After Percutaneous Transluminal Coronary Angioplasty," *Am. J. Cardiol.* 61:67G–70G, 1988, and A. J. R. Black, et al, "Repeat Coronary Angioplasty: Correlates of a Second Restenosis," JACC 11:714–718, 1988.) Restenosis occurs in 25–45% of all patients within 6 months, and attempts to pharmacologically prevent or reduce it using anti-platelet agents, anticoagulants, corticosteroids, and calcium channel blockers have been unsuccessful. Mixed results have been reported with oral fish oil therapy and aggressive lipid reduction. See references cited in "Restenosis After Balloon Angioplasty - A Practical Proliferative Model in Porcine Coronary Arteries," by Robert S. Schwartz, et al, *Circulation* 82(6):2190–2200, December 1990, and "Restenosis and the Proportional Neointimal Response to Coronary Artery Injury: Results in a Porcine Model" by Robert S. Schwartz et al, *J Am Coll Cardiol;* 19;267–74 February 1992, incorporated herein by reference.

Restenosis develops as a consequence of the injury to the arterial wall by the dilation of the balloon in the PTCA procedure. In this procedure, the angioplasty balloon is inflated within the stenosed vessel, or body passageway, in order to shear and disrupt the wall components of the stenosed vessel to obtain an enlarged lumen. With respect to arterial atherosclerotic lesions, the relatively incompressible plaque remains unaltered while the more elastic medial and adventitial layers of the body passageway stretch around the plaque. This process produces dissection, or a splitting and tearing, of the body passageway wall layers, wherein the intima, or internal surface of the artery or body passageway, suffers fissuring. This dissection forms a "flap" of underlying tissue which may reduce the blood flow through the lumen, or block the lumen. Typically, the distending intraluminal pressure within the body passageway can hold the disrupted layer or flap, in place. If the intimal flap created by the balloon dilation procedure is not maintained in place against the expanded intima, the intimal flap can fold down into the lumen and close off the lumen, or may even become detached and enter the body passageway. When the intimal flap closes off the body passageway, often immediate surgery is necessary to correct this problem.

Although the balloon dilation procedure is typically conducted in the catheterization lab of a hospital, because of the foregoing problem, it is always necessary to have a surgeon on call should the intimal flap block the blood vessel or body passageway. Further, because of the possibility of the intimal flap tearing away from the blood vessel and blocking the lumen, balloon dilations cannot be performed upon certain critical body passageways, such as left main coronary artery, which leads into the heart. If an intimal lap formed by a balloon dilation procedure abruptly comes down and closes off a critical body passageway, such as the left main coronary artery, the patient could die before any surgical procedures could be performed.

Additional disadvantages associated with balloon dilation of elastic vascular stenoses is that many fail because of elastic recoil of the stenotic lesion. This usually occurs due to a high fibrocollagenous content in the lesion and is sometimes due to certain mechanical characteristics of the area to be dilated. Thus, although the body passageway may initially be successfully expanded by a balloon dilation procedure, subsequent, early restenosis can occur due to the recoil of the body passageway wall which decreases the size of the previously expanded lumen of the body passageway. For example, stenoses of the renal artery at the ostium are known to be refractory to balloon dilation because the dilating forces are applied to the aortic wall rather than to the renal artery itself. Vascular stenoses caused by neointimal fibrosis, such as those seen in dialysis-access fistulas, have proved to be difficult to dilate, requiring high dilating pressures and larger balloon diameters. Similar difficulties have been observed in angioplasties of graft-artery anastomotic strictures and postendarterectomy recurrent stenoses. Percutaneous angioplasty of Takayasu arteritis and neurofibromatosis arterial stenoses may show poor initial response and recurrence which is believed due to the fibrotic nature of these lesions.

Accordingly, many attempts have been made to develop expandable intraluminal vascular grafts, and methods for expanding the lumen of a body passageway, which prevents recurrence of stenoses in the body passageway, can be utilized for critical body passageways such as the left main coronary artery of a patient's heart, prevents recoil of the body passageway wall, and allows the intraluminal graft to be expanded to a variable size to prevent migration of the graft away from the desired location, and to prevent rupturing and/or erosion of the body passageway by the expanded graft. See, for example, U.S. Pat. Nos. 4,739,762, 4,922,905, and 4,800,882.

Despite the improvement in PTCA and stent technology and procedures, efforts to reduce or eliminate restenosis after PTCA have largely been unsuccessful. In part, these efforts have been hindered by the lack of knowledge of the pathophysiologic mechanisms of human restenosis, and the lack of an accurate animal restenosis model with substantial proliferation. Histologic observation of restenotic tissue from living patients has become readily available with the advent of directional atherectomy. Given this information, there is considerable interest in identification of an animal model similar to human restenosis.

Previous angioplasty animal models have not addressed the proliferative aspects of restenosis directly, instead concentrating on the atheromatous nature of the lesions. The model described by Sanborn has been frequently utilized. (See T. A. Sanborn, et al, "The Mechanism if Transluminal Angioplasty: Evidence for Formation of Aneurysms in Experimental Atherosclerosis," *Circulation* 1983; 78: 654–660.) In this model rabbits fed atherogenic diets have serum cholesterol levels frequently exceeding 1000 mg %. The resulting atheromatous lesions of the aorta, iliac and femoral vessels contain many foam cells in addition to intimal thickening. Although balloon denudation of endothelium increases proliferation, many foam cells are present in contrast to human restenosis. Another model of restenosis in pig carotid arteries involves endothelial denudation with neointimal proliferation. In this model, however, significant proliferative stenosis are not produced unless caused by occluding, organized thrombus. The carotid or iliac arteries of these models contain proportionally more elastin and are elastic vessels, while the coronary arteries contain proportionally more smooth muscle. These non-coronary vessels may thus be less suitable for a coronary artery restenosis model since smooth muscle proliferation is likely a major factor in the genesis of restenosis.

Lack of a practical animal restenosis model has limited the ability to investigate such potential therapies. If such a model were available, it might have the additional benefit of yielding insight into the mechanisms of the restenosis process itself. In "A Practical Proliferative Model in Porcine Coronary Arteries," by Robert S. Schwartz, et al, *Circulation* 82(6):2190–2200, December 1990 and "Restenosis and the Proportional Neointimal Response to Coronary Artery Injury: Results in a Porcine Model" by Robert S. Schwartz et al, *J Am Coll Cardiol;* 19;267–74 February 1992, we describe an experimental animal model of human coronary restenosis developed in domestic swine which accurately mimics the proliferative component of human restenosis, and is practical as well as inexpensive.

SUMMARY OF THE INVENTION

We have found that an experimental animal model of human restenosis may-be developed by the deliberate injury of the coronary vessels of domestic crossbred pigs (Sus scrofa), resulting in proliferative neointimal response occluding or nearly occluding the injured vessel over a period of weeks. The method of the present invention is performed employing a PTCA procedure for advancing a balloon into the desired location within the lumen of the selected vessel, inflating the balloon to a relatively high pressure and diameter, thus expanding and injuring the internal elastic lamina of the vessel.

In the preferred embodiment of the invention, a wire coil is advanced with and over the deflated PTCA balloon to the desired location where it is expanded by the balloon to a diameter exceeding the normal vessel diameter and sufficiently large so that the wires of the coil rupture the internal elastic lamina as well as the media of the vessel.

The damage to the internal elestic lamina, medial layers, and the chronic presence of the coil leads to persistent injury and in turn, causes a proliferation of cells similar to those seen in humans during the restenosis process. The key process is that smooth muscle cells migrate and proliferate from media, through the broken internal elastic lamina, and into the neointima. The proliferation is severe enough to frequently result in luminal compromise, at times complete. Advantageously, the procedure results in proliferation within 28 days, and does not require a hyperlipidemic diet, or any preinjury to the vessel as required by other animal models. The method can be simplified using a combination ketamine/xylazine anesthesia without intubation of the animal, and using local anesthesia for carotid arterial cutdown.

In another embodiment of the invention, the coil may be made with an elongated lead permanently attached to the proximal end of the coil winding and extending away therefrom in a proximal direction and means at a proximal end of the lead remote from the winding for uncoiling the winding to facilitate its removal in an opened condition. This allows the coil to be removed from the lumen following the induced damage to the internal elastic lamina and media, thereby allowing the effect of induced damage to the internal elastic lamina and media to be isolated from the effect of the chronic presence of the coil.

In yet another aspect of the invention the method contemplates employing guide catheters with side holes in order to prevent myocardial ischemia and fibrillation. It is also important to use nonionic contrast agents mixed 1:1 with isotonic saline to prevent ventricular fibrillation.

DESCRIPTION OF THE PREFERRED EMBODIMENTS

Coil Configuration

The coil configuration that was used to produce vessel injury in this model having results reported hereafter was as follows. A length of wire (0.005-in. tantalum or stainless steel) was formed into a to-and-fro pattern so as to remain in a single plane. This structure was then wrapped about the surface of a cylinder-forming mandril either longitudinally or in a serially helical pattern. The diameter of the mandril was comparable with that of an expanded PTCA balloon (3.0 mm). The coil structure was then gradually compressed into smaller and smaller diameters and finally crimped on a fully deflated balloon (roughly 1.4 mm in diameter). The resulting three-dimensional configuration causes multiple wires to be present in a given section perpendicular to the vessel long axis.

Inflation of the balloon results in expansion of the coil to full balloon diameter. This configuration and expansion mechanism are similar to several balloon-expandable intracoronary stent designs including those shown in the '882, '762 and '905 patents, although use of the device to produce the model requires intentional arterial damage inflicted on the vessel wall through gross oversizing.

Figure 1A:
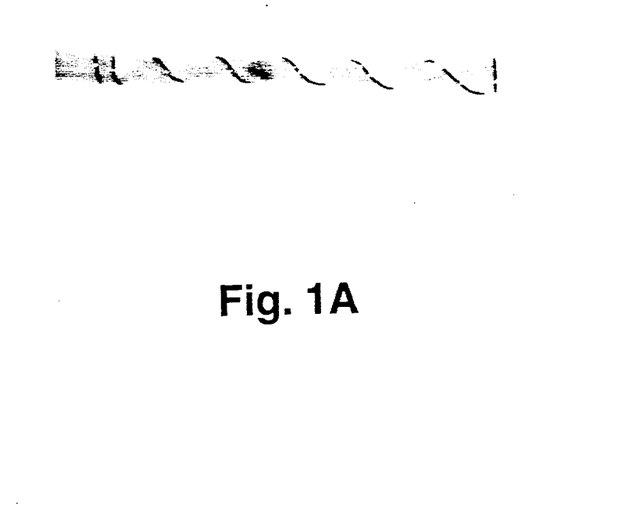
FIGS. 1A to 1C are photographs of the distal end of a PTCA balloon catheter and coiled wire stent in the deflated condition for introduction into the lumen of a selected blood vessel (FIG. 1A), the inflated condition for expanding the lumen and coil (FIG. 1B), and the deflated condition of the balloon for withdrawal (FIG. 1C) leaving the coil in place.
Figure 1B:
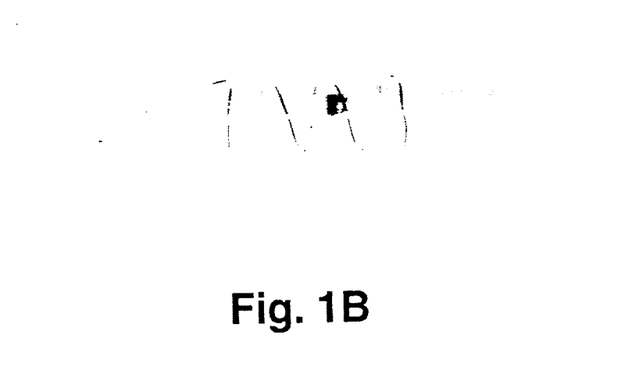
Figure 1C:
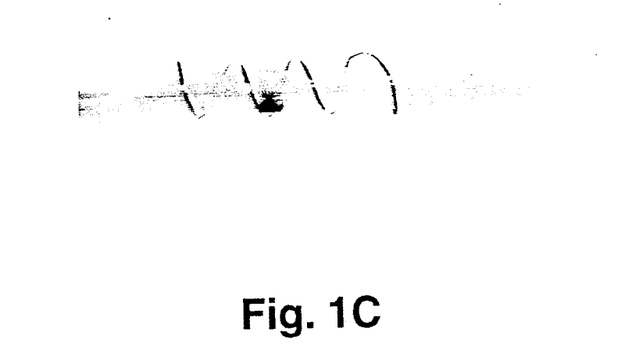

In reference to FIGS. 1A-1C, commercial PTCA balloons (3.0 mm) are wrapped with 0.005" metallic wire (stainless steel or tantalum) such that expanding the balloon (FIG. 1B) will deposit the coil securely in place in a coronary artery (not shown). The balloon size (3.0-3.5 mm) is significantly larger than these pig coronary arteries, which are typically 1.5-2.5 mm diameter.

Implant Procedure

Juvenile pigs (weight 20-30 kg) were obtained from local farmers and fed a standard natural grain diet without lipid or cholesterol supplementation throughout the study.

One day preceding surgery, all pigs are given generic aspirin (650 mg) to prevent death from platelet-induced coronary arterial occlusion, and nifedipine XL 30 mg to help alleviate coronary artery spasm after implant. All pigs undergo intramuscular injunction of ketamine 12 mg/kg and xylazine 8 mg/kg for anesthesia. No endotracheal intubation is necessary. They are placed supine, and the ventral neck region infiltrated with xylocaine 1% (total dose 10 ml) for local anesthesia. Continuous electrocardiographic and noninvasive, percutaneous hemoglobin saturation monitoring performed. Either external carotid artery is exposed and an 8 French arterial sheath is placed for arterial access. Heparin (10,000 units) is administered intro-arterially as a bolus.

It is essential to have side holes in the guide catheter to prevent damping and subsequent ventricular fibrillation (a lethal rhythm, easily produced if care is not taken). It is also critical to have nonionic contrast, which we mix 1:1 with saline to help avoid ventricular fibrillation also.

To engage the left main coronary artery from either carotid artery, a standard right Judkins JR4 curve is used. Conversely, to engage the right coronary artery, a standard left JL4 curve was used. Thus, the left/right engagement methods are reversed from those used in the human femoral artery approach.

The left main or right coronary artery is intubated using standard technique and known guide catheter curves with an 8 French PTCA guide catheter under fluoroscopic visualization.

The balloon/metallic coil device is advanced into either the left anterior descending, circumflex, or right coronary artery over a standard 0.014 inch PTCA guide wire. The balloon is inflated (FIG. 1B) once to high pressure (6-14 atm), deflated (FIG. 1C), and removed. Another bolus of heparin (5000 units) is then administered intravenously. Fluoroscopy and selective contrast injection confirm both vessel patency and coil location. Repeat angiography is performed at 15 minutes to confirm vessel patency. The carotid vessel may be repaired using standard technique or ligated, and the neck wound closed with interrupted sutures. The animals are returned to quarters and closely observed for 28 days.

There is no need for postoperative analgesia, as the local anesthetic remains in place for a few hours, and the cutdown procedure otherwise is quite comparable to that done on humans. Humans need no analgesics typically after this cutdown. No anti-platelet agents are used except the asprin used during the one day pretreatment regimen. Multiple arteries within the same heart can be similarly implanted to make maximal use of a given animal.

To determine the response of the coronary vessels to oversized, hyperbaric balloon inflation only (without coil implant), the procedure performed as reported in "A Practical Proliferative Model in Porcine Coronary Arteries," by Robert S. Schwartz, et al, *Circulation* 82(6):2190-2200, December 1990, identically except that a PTCA balloon was used without a metallic coil mounted on it. This latter procedure was performed in five pigs. An additional three pigs underwent coil implantation in which the coil was matched more closely to the vessel diameter, in an effort to establish the fact that oversizing the coil is an essential part in the production of medial injury and vessel response.

Histopathology

In our experience reported in "A Practical Proliferative Model in Porcine Coronary Arteries," by Robert S. Schwartz, et al, *Circulation* 82(6):2190-2200, December 1990, and in part in our abstract entitled "A Practical Porcine Model of Human Coronary Artery Restenosis Post PTCA" appearing in JACC, Vol. 15, No. 2, February 1990, p. 165A, eleven animals underwent successful coil implantation. During this same time period of successful implants, coil implantation attempts were made in an additional eight pigs, all of which died acutely (within 6 hours of implantation) for the following reasons: there were four anesthetic and procedural deaths and four deaths related to severe coronary artery injury by the coil itself. Overall survival was thus 11 of 19, or 58%. All had patent vessels, determined angiographically at 15 minutes after coil implant. The nine pigs were sacrificed at times from 28 to 70 days using intravenous barbiturate and potassium chloride euthanasia. In our reported experience, two pigs died spontaneously at 9 and 11 days after coil implant.

Hearts were removed immediately and perfusion-fixed at 100 mm Hg for 24 hours with 10% neutral buffered formalin. Coronary artery segments containing the metal coils were easily identified externally, and were carefully removed along with at least 1 cm of normal vessel proximal and distal to the coil. Gross sectioning of the fixed vessels is performed at 2 mm increments perpendicular to the vessel axis. Coils are left in place, and cutting is done with sharp, hardened scissors. Individual coil wires are cut first, followed by the arterial tissue. This method results in minimal vessel size and shape distortion prior to embedding in standard paraffin block. Each arterial segment was embedded and stained with hematoxylin-eosin, and Lawson's elastic-van Gieson stains. Immunohistochemical stains including action, desmin and vimentin were performed on a subset of three pigs.

Each 2-mm histologic section was examined to determine the site of maximal lumenal narrowing for a given artery. The section with the most severe stenosis was used to measure the following parameters: thickness of vessel media, major and minor axes of the native vessel lumen (measured from internal elastic lamina to internal elastic lamina across the largest and smallest diameters), and major and minor axes of the stenotic lumen (residual lumen diameters). Percent area stenosis was calculated assuming the lumen to be an ellipse (area=pi×major axis÷2×minor axis÷2). Measurements were made microscopically using a calibrated eyepiece reticule.

All sections were examined by an experienced cardiac pathologist for comparison to human restenosis tissue in regard to cell type, architecture, and amount of ground substance. The human tissue for comparison was obtained previously from patients undergoing directional coronary atherectomy for the treatment of restenosis.

Results

Of the eleven pigs that survived the procedure, two animals died prior to sacrifice, at 9 and 11 days respectively after coil implantation. At autopsy both of these animals showed extensive proliferative neointimal tissue with severe stenosis of the vessel lumen. No acute thrombus was observed in either animal at the site of the coil induced stenosis. It was thus assumed that these severe stenoses rendered each heart ischemic during normal activity and caused a fatal arrhythmia. In the pig heart, vulnerability to ischemic ventricular fibrillation is well known, and presumably relates to a lack of collateral circulation. The remaining 9 animals survived without complication or clinically apparent problem until sacrifice:

TABLE I

| Animal Number | Days Survived | Mode Coil of death | Coil Material | Location |
|---|---|---|---|---|
| 1 | 531 | 67 | Sacrificed | Tantalum | RCA |
| 2 | 533 | 53 | Sacrificed | Stainless | LAD |

TABLE I-continued

| Animal Number | Days Survived | Mode Coil of death | Coil Material | Location |
|---|---|---|---|---|
| 3 | 590 | 69 | Sacrificed | Tantalum | RCA |
| 4 | 592 | 70 | Sacrificed | Stainless | LAD |
| 5 | 595 | 69 | Sacrificed | Stainless | LAD |
| 6 | 637 | 11 | Spontaneous | Stainless | LAD |
| 7 | 641 | 57 | Sacrificed | Tantalum | CX |
| 8 | 772 | 28 | Sacrificed | Tantalum | CX |
| 9 | 773 | 28 | Sacrificed | Stainless | LAD |
| 10 | 775 | 28 | Sacrificed | Tantalum | CX |
| 11 | 780 | 9 | Spontaneous | Tantalum | LAD |

Figure 2:
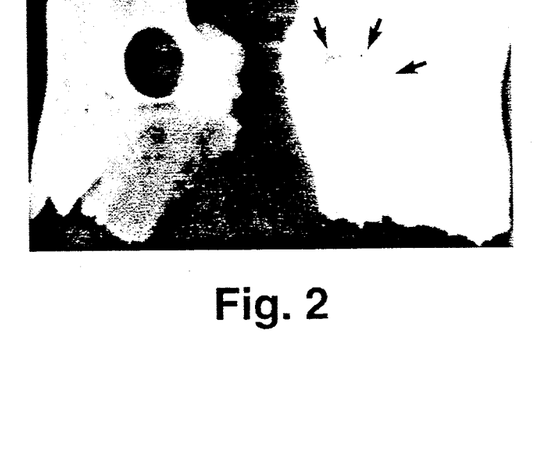
FIG. 2 is a gross photograph of the lumenal compromise resulting from the metallic coil placement (L, lumen; NI, neointima M, media, holes from wires).

Abbreviations:
Stainless - Stainless Steel
LAD - Left Anterior Descending Coronary Artery
CX - Circumflex Coronary Artery
RCA - Right Coronary Artery Light microscopy in all animals revealed a proliferative neointimal response of varying magnitude. FIG. 2 demonstrates cross stenosis caused by the proliferative neointima in the right hand tissue section.

These cut sections were taken from the same left anterior descending coronary artery, within 3 mm of each other. The implantation of coil wires is shown in the proliferative section (arrows, right), while a normal appearing vessel is seen where there were no coil wires (left). The proliferation induced by the injury nearly obliterated the lumen of this vessel, resulting in a severe stenosis.

Figure 3:
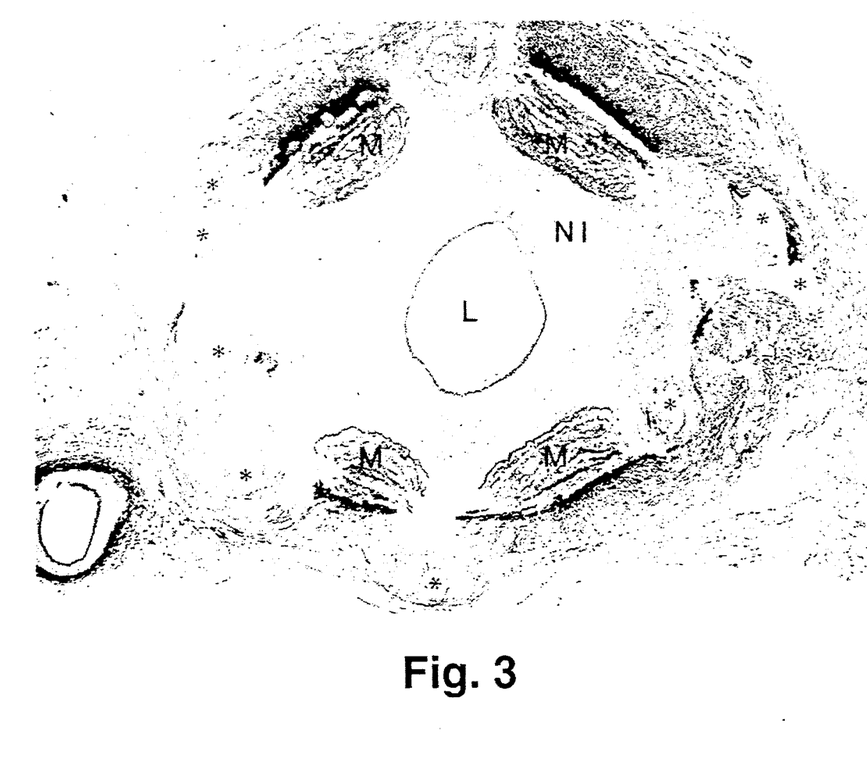
FIG. 3 is a photomicrograph section showing gross neointimal proliferation luminal compromise and destruction of internal elastic lamina by coil wires.

In all animals, rupture of the internal elastic lamina by at least some of the metallic coil wires was evident, and the coil usually resided in the vessel media. FIG. 3 shows a low-power photomicrograph of another stenotic segment. Rupture of the internal elastic lamina is evident, and the coil wires have been driven entirely through the vessel media. A thick neointima is present, causing significant luminal stenosis. Mild chronic inflammation was usually evident around each coil wire. No qualitative histopathologic differences were noted between the tantalum-implanted versus the stainless steel-implanted vessels.

Figure 4:
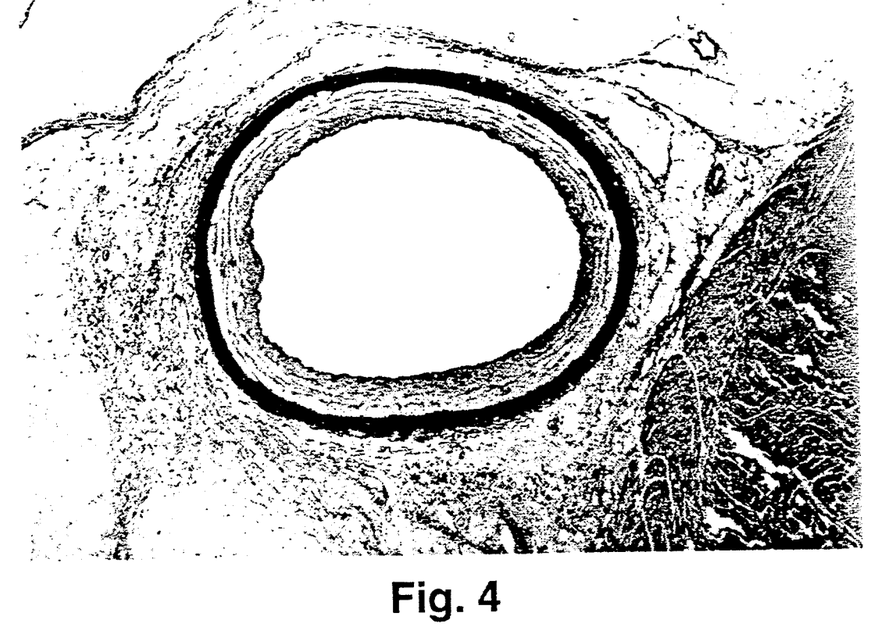
FIG. 4 is a normal section of coronary artery taken adjacent to a segment with coil placement showing intact internal elastic lamina.
Figure 5:
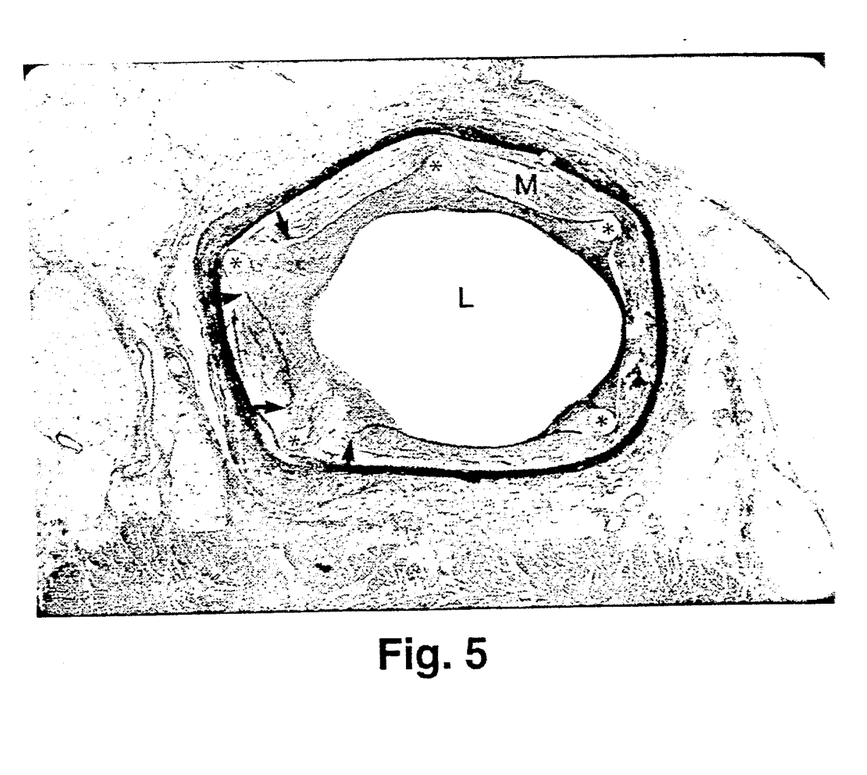
FIG. 5 is a microscopic section (low power) in a case where fortuitously, not all coil wires penetrated into the vessel media.

A normal vessel proximal to coil placement is shown for reference in FIG. 4. Mild chronic inflammation was usually evident around each coil wire. FIG. 5 is of particular interest because not all wires ruptured the internal elastic lamina. The greatest degree of proliferation resulted from the two coil wires which ruptured the internal elastic lamina, with neointima growing to confluence between them in the vessel lumen. On the contralateral side of the vessel however, the lamina remained intact, media was not entered, and substantially less smooth muscle cell proliferation is seen. At the bottom portion of this section, normal media without any proliferation is seen. This is the segment with the greatest separation of coil wires.

Table II shows the stenotic and native lumen sizes, thicknesses of proliferative tissue, and resulting percent area stenosis:

TABLE II

| Animal Number | Percent Area Stenosis* | Native Lumen | | | Stenotic Lumen | | |
|---|---|---|---|---|---|---|---|
| | | Diameter (mm) | | Area (mm2) | Diameter (mm) | | Area (mm2) |
| | | Maj | Min | | Maj | Min | |
| 1 | 531 | 75% | 1.74 | 1.71 | 2.34 | 0.99 | 0.75 | 0.58 |
| 2 | 533 | 70% | 2.94 | 2.85 | 6.58 | 1.65 | 1.53 | 1.98 |
| 3 | 590 | 19% | 2.19 | 1.62 | 2.78 | 1.98 | 1.47 | 2.29 |
| 4 | 592 | 86% | 2.34 | 1.38 | 2.54 | 0.87 | 0.51 | 0.35 |
| 5 | 595 | 50% | 2.70 | 2.52 | 5.35 | 2.43 | 1.41 | 2.69 |
| 6 | 637 | 72% | 1.35 | 1.08 | 1.15 | 0.75 | 0.54 | 0.32 |

TABLE II-continued

| Animal Number | Percent Area Stenosis* | Native Lumen | | | Stenotic Lumen | | |
|---|---|---|---|---|---|---|---|
| | | Diameter (mm) | | Area (mm2) | Diameter (mm) | | Area (mm2) |
| | | Maj | Min | | Maj | Min | |
| 7 | 641 | 94% | 1.89 | 1.44 | 2.09 | 0.45 | 0.36 | 0.13 |
| 8 | 772 | 50% | 1.95 | 1.74 | 2.67 | 1.32 | 1.29 | 1.34 |
| 9 | 773 | 99+% | 3.36 | 2.67 | 7.05 | 0.09 | 0.06 | 0.005 |
| 10 | 775 | 99% | 2.46 | 2.01 | 3.88 | 0.3 | 0.18 | 0.04 |
| 11 | 780 | 77% | 2.40 | 2.13 | 4.01 | 1.41 | 0.84 | 0.21 |

*Percent area stenosis = 100 × [1.00 − (stenotic area ÷ native vessel area)] = 100 × [1.00 − [(pi × stenotic major axis × stenotic minor axis ÷ 4) ÷ (pi × native major axis × native minor axis ÷ 4)]].
Vessel area = pi × major axis ÷ 2 × minor axis ÷ 2.

Figure 6:
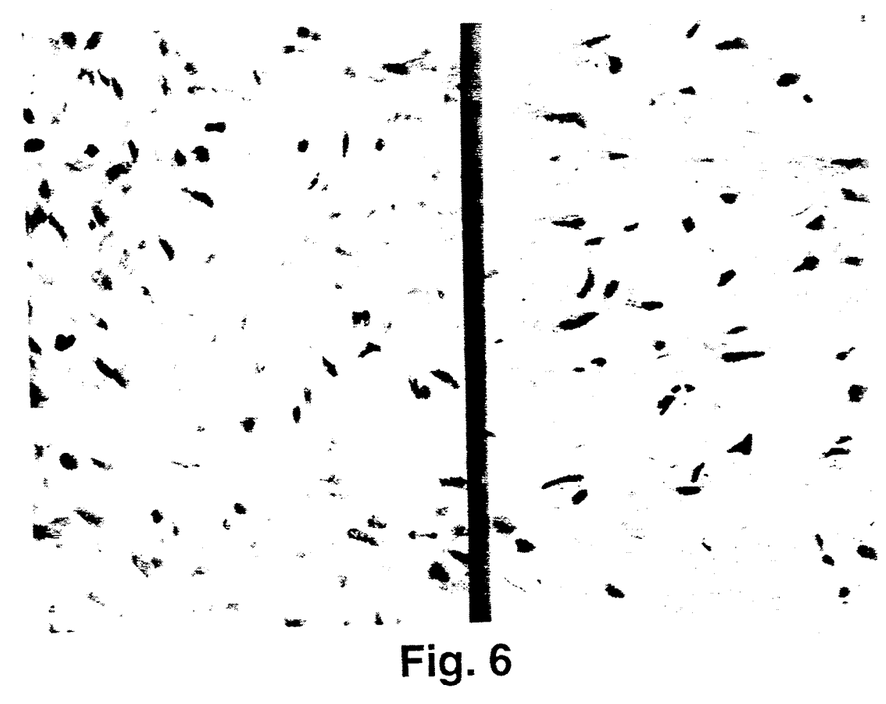
FIG. 6 is a high power side-by-side comparison of a representative sample of human restenosis (left) and tissue from the porcine restenosis model.

When examined under higher power, the histologic characteristics of this proliferation are identical to that of tissue obtained from humans who had angiographic restenosis post PTCA and underwent directional atherectomy with the Simpson/DVI catheter. FIG. 6 is a side-by-side high power microscopic comparisons of the pig proliferative tissue (right panel) and a representative sample of human restenosis tissue (left panel). That these tissues (human and porcine) are virtually identical is evident in terms of cellular appearance, cell density, and amount and character of intercellular ground substance. Immunohistochemical stains (action, desmin, and vimentin) showed these proliferative cells were of smooth muscle origin, evidenced by the strong presence of action and vimentin, and significantly less desmin.

Balloon Inflation Only

Five additional pigs underwent oversized, overpressured balloon inflation only, without coil implantation. Table III shows results from this series:

TABLE III

| Animal Number | Percent Area Stenosis* | Native Lumen | | | Stenotic Lumen | | |
|---|---|---|---|---|---|---|---|
| | | Diameter (mm) | | Area (mm2) | Diameter (mm) | | Area (mm2) |
| | | Maj | Min | | Maj | Min | |
| 1 | 54 | 2.04 | 1.89 | 3.03 | 2.04 | 0.87 | 1.39 |
| 2 | 29 | 3.09 | 1.68 | 4.08 | 3.09 | 1.20 | 2.91 |
| 3 | 100* | 3.15 | 1.29 | 3.19 | 0.00 | 0.00 | 0.00 |
| 4 | 0 | 3.21 | 2.28 | 5.74 | — | — | — |
| 5 | 0 | 2.94 | 2.19 | 5.05 | — | — | — |

Percent area stenosis = 100 × [1.00 − (stenotic area native vessel area)] = 100 × [1.00 − [(pi × stenotic major axis × stenotic minor axis ÷ 4) ÷ (pi × native major axis × native minor axis ÷ 4)]].
Vessel area = pi × major axis ÷ 2 × minor axis ÷ 2.
*Thrombotic occlusion.

Figure 7:
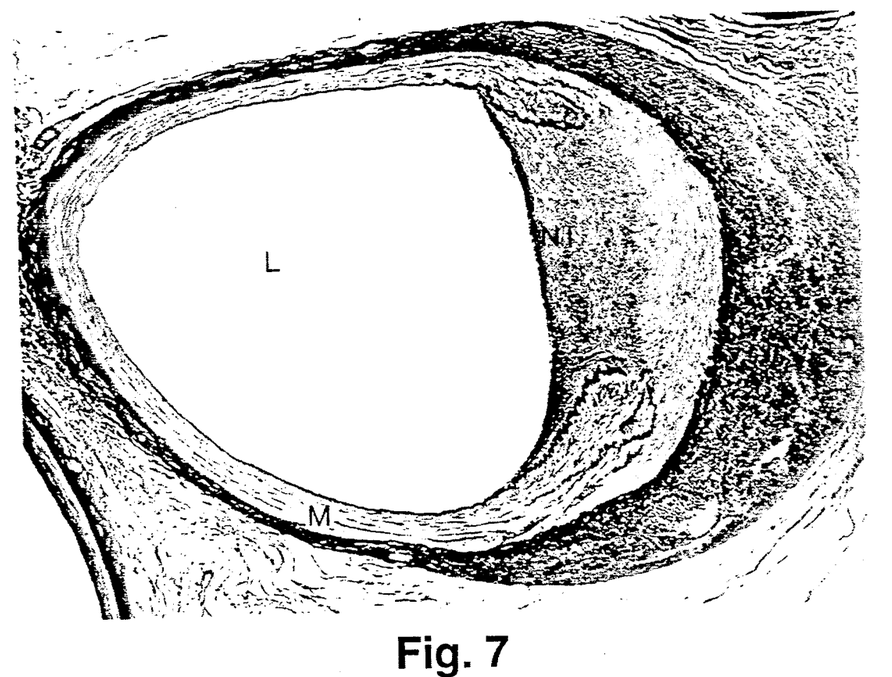
FIG. 7 is a representative section from one pig that underwent inflation of the artery only, without coil implant and showing less obstructive neointima.

Three of these five pigs had a proliferative response to deep medial injury although the percent stenosis was somewhat less in two. In one pig, there was complete occlusion, but this was from acute thrombosis and, in retrospect, represented excessively severe oversizing of the balloon to the vessel (a small diagonal artery). The remaining two pigs had little or no proliferation seen. FIG. 7 depicts one of the two vessels that underwent proliferation and moderate luminal obstruction.

Mean Injury Scores

In a second series of tests reported in "Restenosis and the Proportional Neointimal Response to Coronary Artery Injury: Results in a Porcine Model" by Robert S. Schwartz et al, *J Am Coll Cardiol;* 19;267-74 February 1992, we established a mean injury scoring system for the injury caused by the coil wires. Vessel injury at every wire site was determined by the anatomic vessel structures penetrated by each wire. A numeric value was assigned according to injury severity. This value could vary from 0 (least injury) to 3 (most injury) according to the following criteria:

TABLE IV

| Score | Description of Injury |
|---|---|
| 0 | Internal elastic lamina intact; endothelium typically denuded; media typically compressed but not lacerated |
| 1 | Internal elastic lamina lacerated; media typically compressed but not lacerated |
| 2 | Internal elastic lamina lacerated; media visibly lacerated; external elastic lamina intact but compressed |
| 3 | External elastic lamina lacerated; typically large lacerations of media extending through the external elastic lamina coil wires sometimes residing in adventitia |

Neointimal thickness at each wire was also measured to determine the response to the injury.

The mean injury score for the coil segment was the sum of the scores achieved for each wire divided by the number of coil wires present in the segment. The mean neointimal thickness for all wire sites in the section was used as the index of injury response. After the mean injury and response were calculated, linear regression was performed by standard methods to derive a slope, an intercept and Pearson correlation coefficient for the relations.

Figure 9:
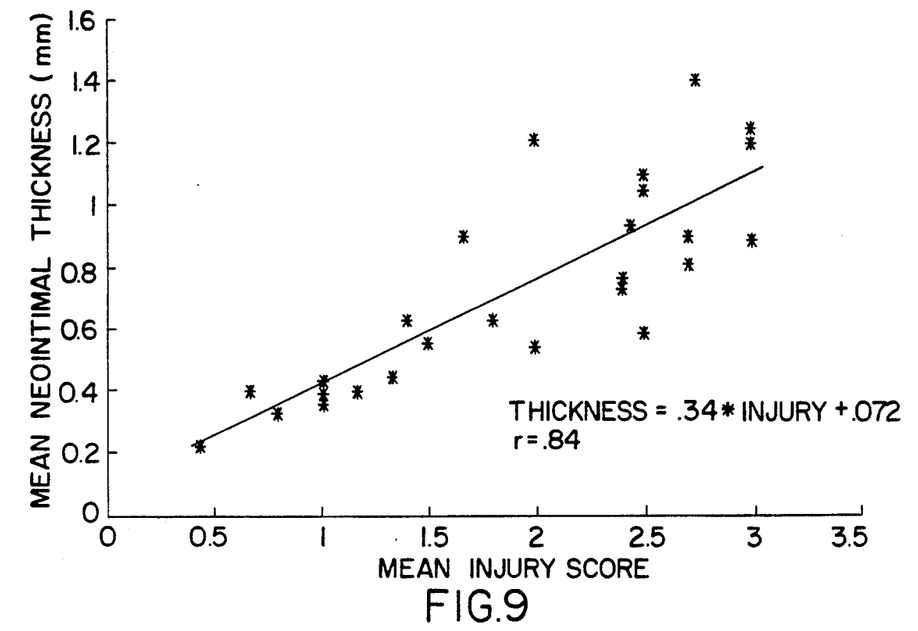
FIG. 9 is a scatterplot of mean neointimal thickness versus mean injury score for 26 coil-injured coronary artery segments.
Figure 10:
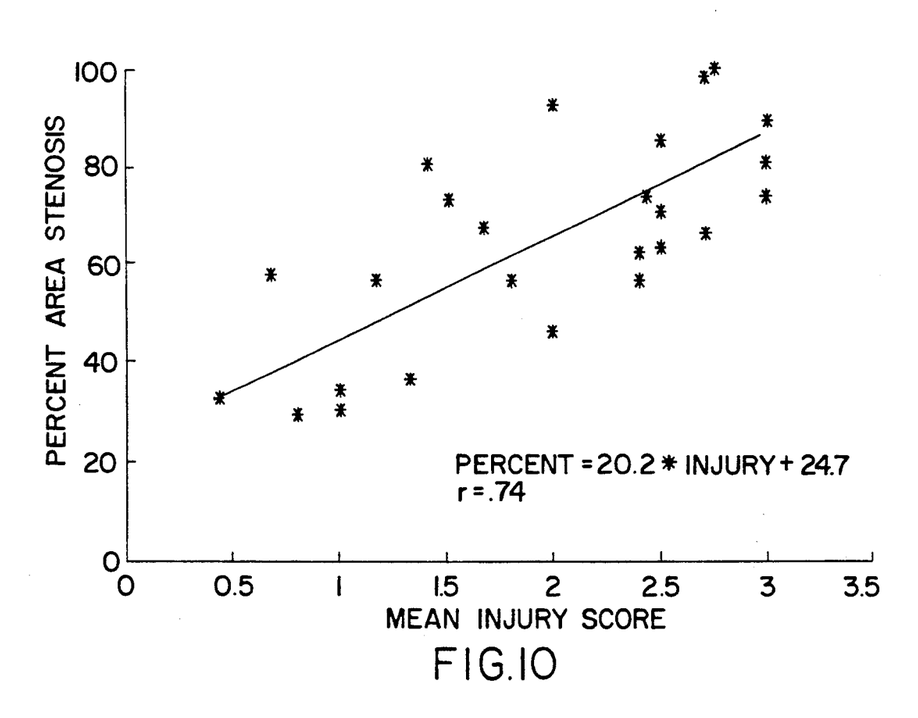
FIG. 10 is a scatterplot of mean percent area stenosis versus mean injury score for 26 coil-injured coronary artery segments.
Figure 11:
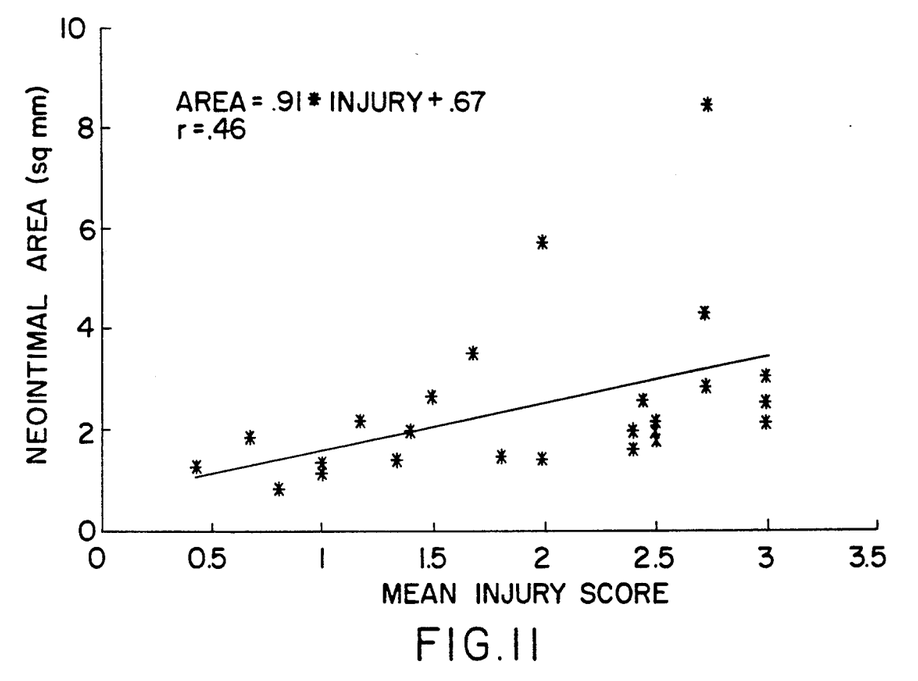
FIG. 11 is a scatterplot of absolute neointima area stenosis versus mean injury score for 26 coil-injured coronary artery segments.
Figure 12:
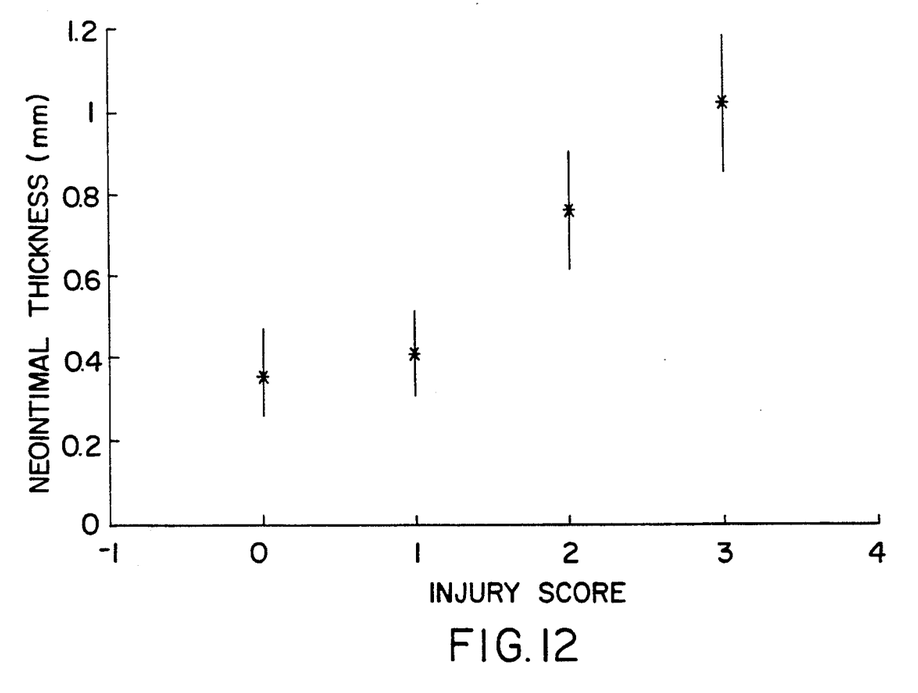
FIG. 12 is a graph of neointimal thickness (and standard deviation) as a function of wire injury depth (0 through 3) for all wires measured.
Figure 13:
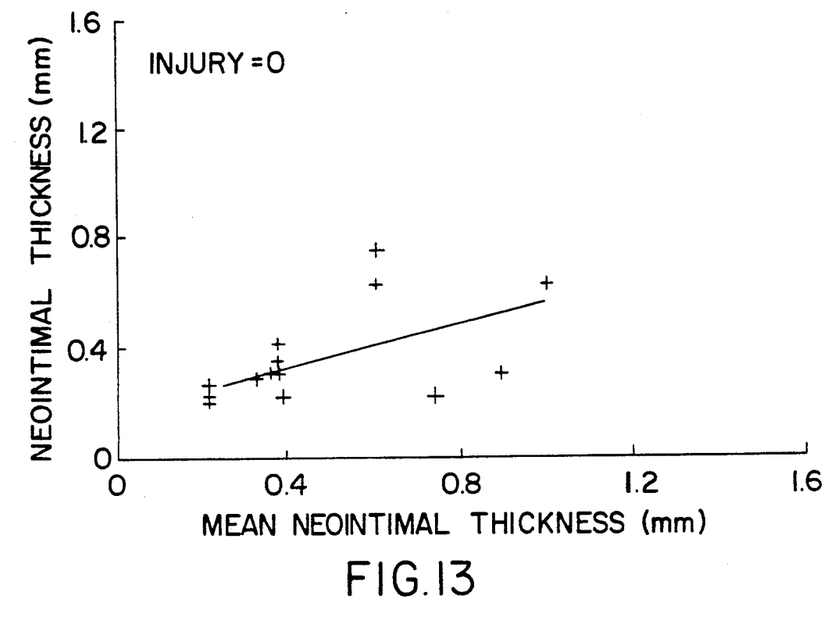
FIGS. 13-16 are graphs of neointimal thickness for each level of injury (0 to 3) at each wire site.
Figure 14:
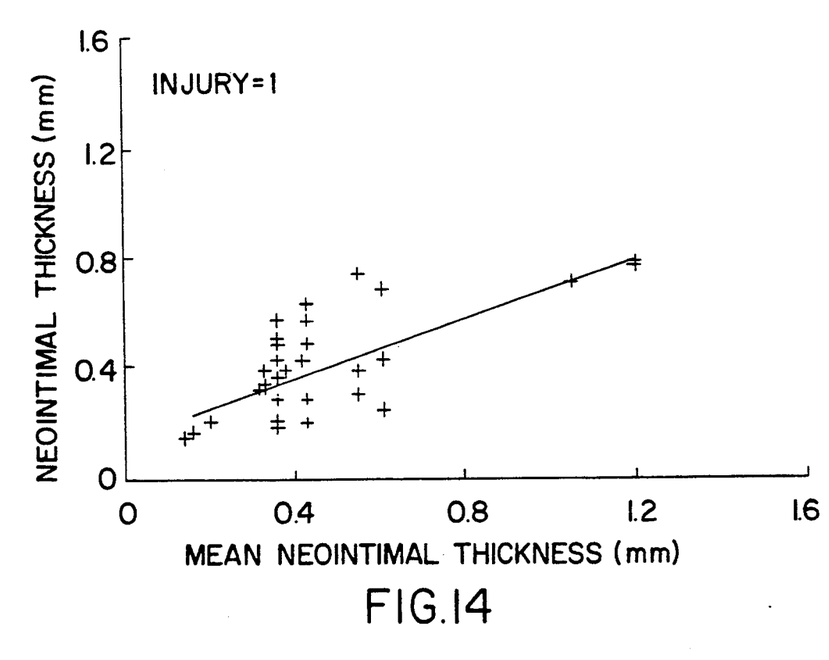
Figure 15:
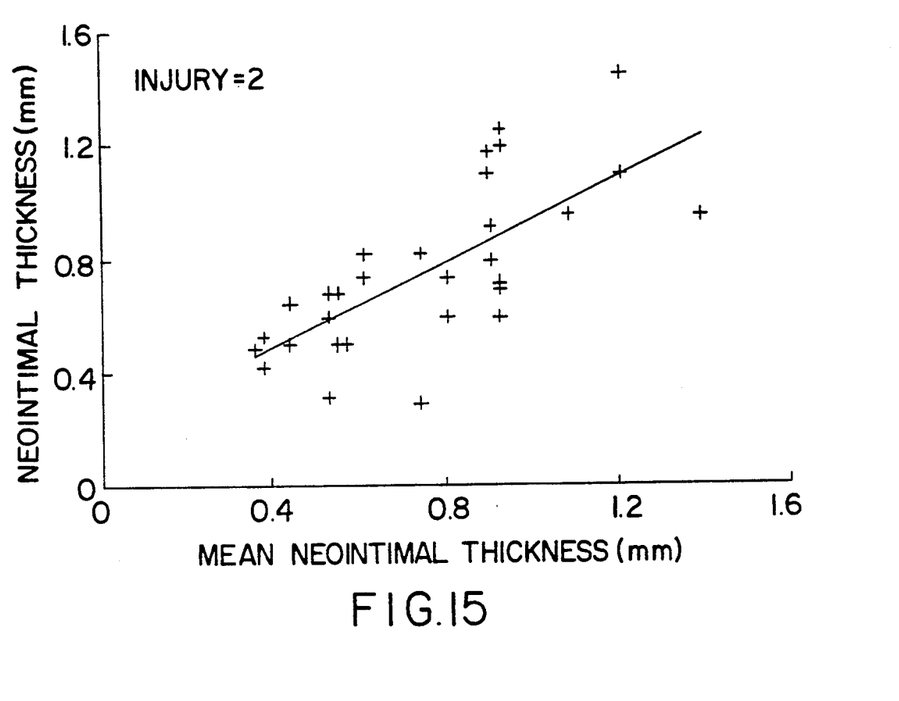
Figure 16:
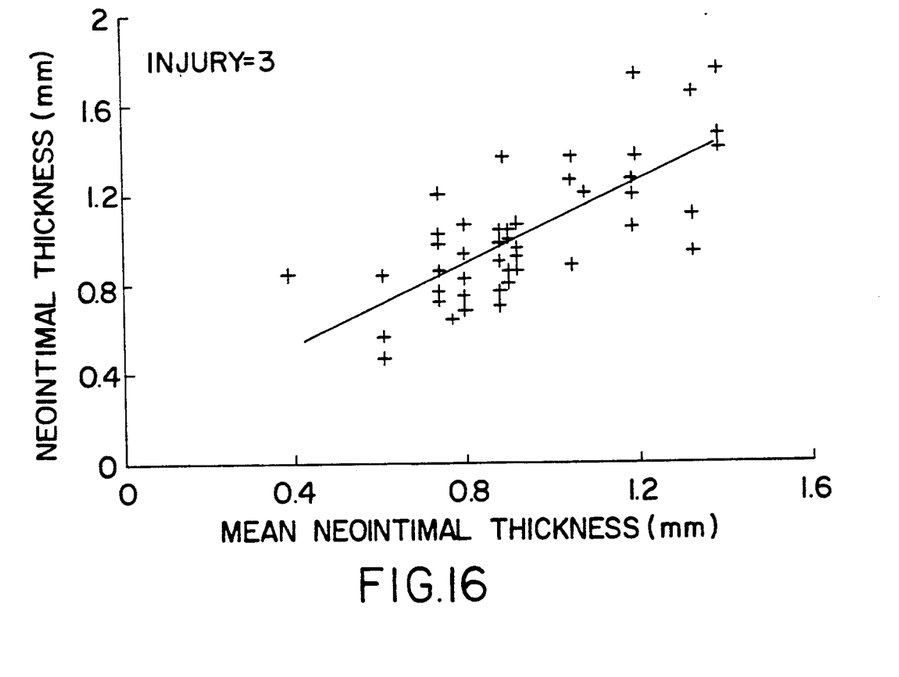

The results are shown in FIGS. 9-16. FIGS. 9-11 show plots of neointimal thickness, percent area stenosis and neointima area versus mean injury score for each injured segment. A statistically siginficant proportional relationship existed in all cases. FIG. 12 shows neointimal thicknesses for all wire sites individually (as opposed to mean thickness) plotted versus mean injury score for the segment observed. FIGS. 13-16 show the relation between the mean neointimal thickness for all seqments analyzed versus neointimal thickness at individual wire sites within that section. They show that proliferation at a single wire site was correlated with the overall injury present at that site. These relations are statistically significant for all degrees of injury. Therefore, as documented in this model, all injured vessels develop neointima of variable thickness related to the degree of injury. Neointima at sites with more overall injury grew confluently and thus may have caused proliferation at the milder injury sites (as shown by FIGS. 13-16). These combined results support the idea that the vessel injury caused by the wire, and not the wire material itself, is responsible for most of the neointimal growth.

The structural integrity of the internal elastic lamina appears essential to minimize neointimal proliferation. Therefore, in order to provide a porcine model for restenosis treatment of injured coronary arteries, the internal elastic lamina is ruptured by the coil wire to expose medial tissue to flowing blood. This consistently initiates restenosis in the porcine model and provides a basis for evaluating restenosis treatments that may be beneficial in treating human coronary artery injury. The examination of a blood vessel for restenosis can therefore be conducted by sectioning the blood vessel at the point where the wire stent was applied, measuring the degree of injury to the blood vessel in the section, measuring the neointimal thickness in the section and then comparing the neointimal thickness with the degree of injury. The statistical measures of injury and restenosis provided by this method of examination allows for a statistical comparison of the efficacy of various restenosis treatments.

Coil Implantation, Not Oversized

Figure 8:
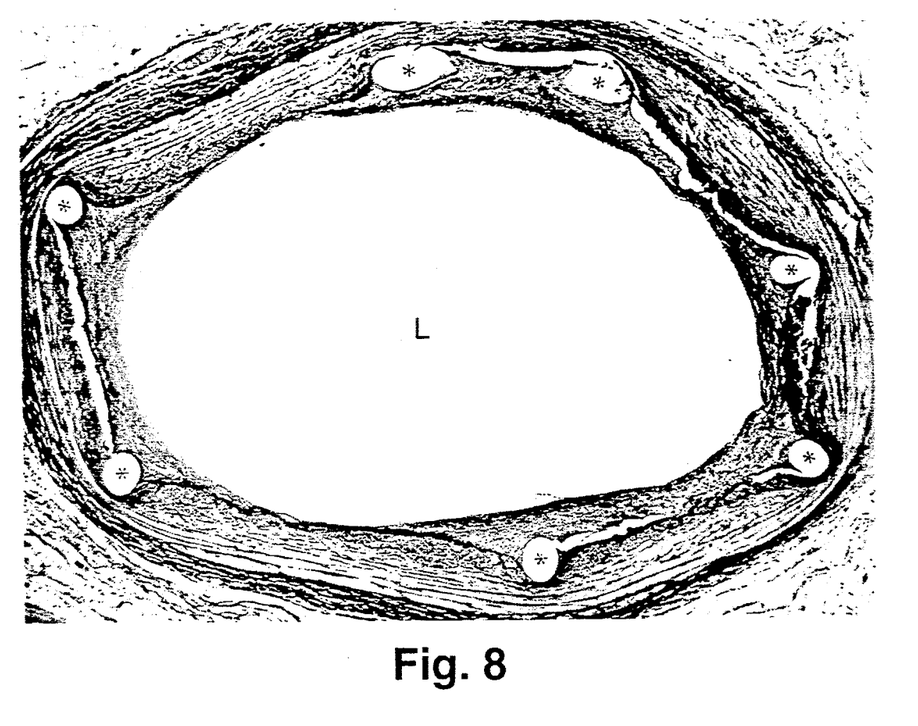
FIG. 8 is a section from one pig in which the coil was sized more appropriately to the vessel lumen resulting in little injury and consequently, much less obstructive neointima.

The three pigs with coil implantation in which coil size was closely matched to vessel size did not exhibit appreciable proliferation. FIG. 8 shows the minimal amount of neointimal proliferation in a representative animal from this group.

Medial Injury and Restenosis

The inventive model results in proliferative lesions histologically identical to human restenosis, in contrast to prior animal models and thus mimics the injury induced by PTCA with extensive medial injury. Oversizing the balloon for the target vessel results in severe elevations in vessel wall tension. This is followed by chronic tension in the medial smooth muscle due to the wire coil. Some degree of foreign body irritation likely results from the wire coil itself. The small diameter wire on the surface of the balloon results in extreme shear stresses from the small radius of curvature of the wire. Many wires thus penetrate the internal elastic lamina, located in the media rather than simply circumferentially distending the vessel.

FIG. 5 strongly suggests that extensive smooth muscle proliferation is a response to rupture of the internal elastic lamina and consequent medial injury. In this section, the farthest left coil wires did penetrate media, and resulted in more substantial proliferation. Conversely, the farthest right wires did not, and proliferation of only a few cells thickness is evident. The segment of vessel at the lowermost portion of FIG. 5 is entirely normal, although this segment was stretched by the balloon. This segment has the farthest distance between any coil wires. Rupture of the internal elastic lamina during PTCA, medial laceration and subsequent restenosis has been documented in humans. Mechanical medial injury is a known factor in generating a proliferative response. It is evident that simple over-distension of the vessel wall alone does not produce the most intense proliferation in this model, since portions of the vessel media which were stretched but not penetrated by wire exhibit mild or no proliferation. This model suggests that lacerations or splits of normal media may contribute significantly to the genesis of restenosis.

Role of Lipids in Restenosis

In contrast to primary atheromatous lesions, the human restenotic lesion consists of a vigorous proliferation of smooth muscle cells which have likely migrated from damaged media into the lumen as part of the reparative process. The proliferative nature of the restenotic lesion thus differs distinctly from the original atherosclerotic disease. The time course of restenosis is significantly shorter, also suggesting a different mechanism.

No atherogenic diet was fed to these animals. The production of histology resembling restenotic morphology without hyperlipidemia also supports the concept that restenosis is a process independent from atherosclerosis. Hyperlipidemia might intensify the observed proliferative response, a possibility not tested in this study. Although the proliferative effects might have been promoted further with a high cholesterol diet, hyperlipidemia is clearly not a necessary condition for production of the proliferative response in this model.

Foreign Body Response

Stainless steel and tantalum are relatively biologically inert materials. However, both stimulated restenosis tissue in this model. This may be from chronic, severe mechanical tension placed on the vessel due to the oversized coil expansion, from a foreign body reaction, or both. Since only minimal amounts of chronic inflammation was observed in this model, it is likely that inflammation was a lesser factor in stimulating proliferation.

Platelets and Thrombus

The role of platelets and thrombus is not well defined in the current model. In the hyperlipidemic rabbit iliac artery, a statistically significant reduction in "restenosis" was found when anti-platelet agents were used following balloon dilation of a stenotic segment. Platelet deposition and release of growth factors may play a role in the genesis of this model; it was for this reason that no antiplatelet agents were used except for the asprin used in the one day pre-treatment regimen. Platelet deposition and thrombus at the site of medial injury and on the coil itself would be expected in this model. This deposition could be a factor responsible for the proliferation of smooth muscle cells. Prior reports suggest that endothelial regrowth protects against platelet-thrombus deposition. It is therefore possible that in the initial days after angioplasty when endothelium and neointima are forming may be critical in the genesis of the proliferative response. Aspirin pretreatment of these pigs during the procedure and after coil implant might have diminished the proliferative response.

In the current model, the foreign body coil may have slowed or prevented endothelial regrowth. There might thus have been longer exposure of media to blood elements which increased the amount of platelet deposition, thrombus, and consequent cellular proliferation. Acute studies in this model should be examined to establish the degree of thrombus at the site of injury.

Implications for Coronary Artery Stents

The analogy implications of the metallic coil implanted in this model to generate restenosis, and the current clinical tests of self expanding or balloon expandable metallic stents intended to prevent restenosis of the type shown in the above referenced patents are clear. The proliferative response in this pig model resulted from intentional, severe oversizing and overinflating the balloon on which the coil was mounted. The intent in this model was to injure media to stimulate a vigorous healing response.

The neointimal tissue covering stents in experimental stent placement is likely a mild foreign body response, but has never been shown to proliferate as severely as noted in this model.

In order to address the issue of foreign body response, it is also possible in one embodment of the model to remove the coiled stent at a preselected time following the initial media injury. This can be accomplished through the use of a coiled stent such as that disclosed in U.S. Pat. No. 4,886,062 issued to Wiktor (which is hereby incorporated by reference) which has been modified to include a withdrawl feature. For example, a coiled stent with a withdrawl feature can be used as shown in FIGS. 17–20.

Figure 17:
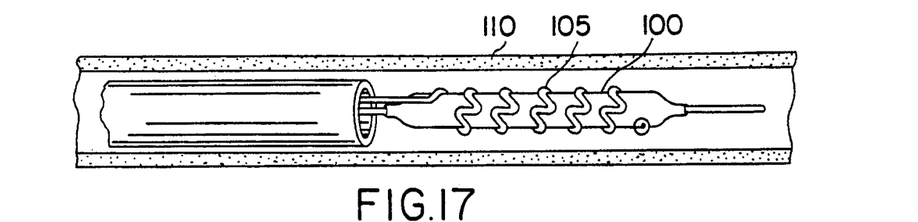
FIG. 17 is a side elevation of an embodiment of the invention in which a coiled stent on a balloon is placed into a blood vessel.
Figure 18:
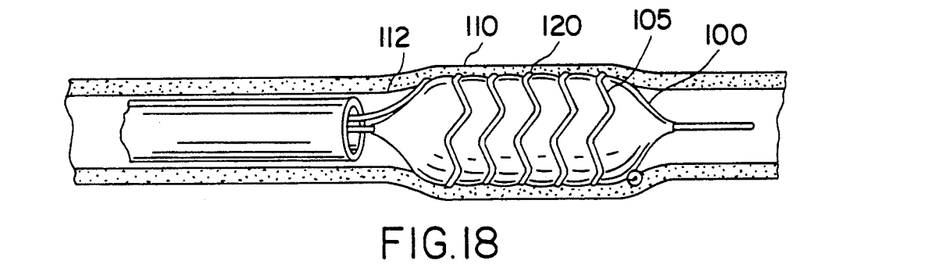
FIG. 18 is a side elevation as in FIG. 17 with the balloon inflated to expand the coiled stent against the wall of the blood vessel and through the internal elastic lamina.
Figure 19:
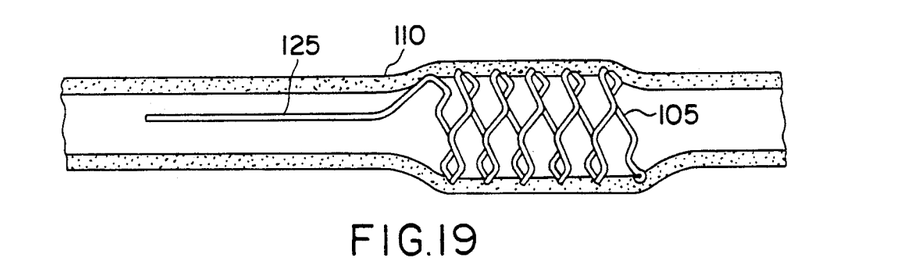
FIG. 19 is a side elevation as in FIG. 18 with the balloon removed to leave the coiled stent in place.

In FIG. 17 it is seen how balloon 100 and stent 105 are directed to a desired position in an artery 110, balloon 100 still being deflated. Once the desired position is achieved, balloon 100 is inflated using standard angioplasty procedures and techniques except that oversizing of the stent 105 to produce medial injury is deliberately employed. It should be noted in FIGS. 17-20 that the expansion shown is merely illustrative of the method used and not drawn to scale so that they should not be regarded as showing the amount of oversizing required in the present invention. That can be readily determined experimentally by one skilled in the art by producing the desired medial damage in the vessel 110. As balloon 100 expands, so does stent 105 as shown in FIG. 18. The expanding balloon 100 together with stent 105 contacts the vessel wall 112, expands the vessel 110 and provides the desired medial injury by forcing the wires of the stent through the elastic lamina of the vessel wall 112 at their point of contact 120. With the expansion completed, balloon 100 is deflated and withdrawn leaving stent 105 implanted within the vessel 110. The stent 105 can then be allowed to remain in the vessel 110 in an expanded condition for the period of time desired, typically several minutes. An elongated lead 125 can be merely left in place, extending in a proximal direction from the end of the stent 105.

Figure 20:
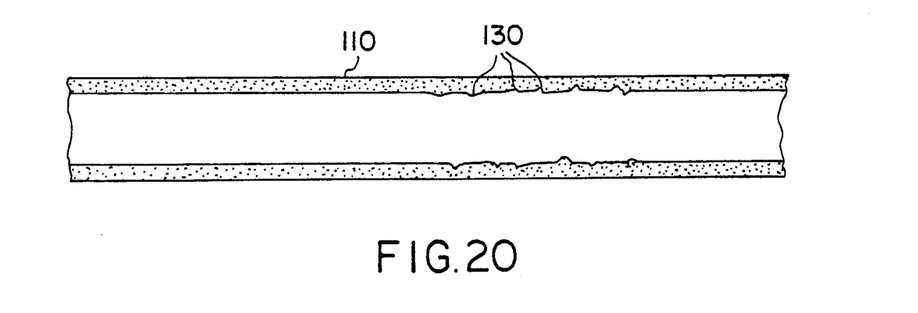
FIG. 20 is a side elevation as in FIG. 19 with the coiled stent removed showing the damaged vessel intima.

When removal is desired, grasping the proximal end of elongated lead wire 125 and gently pulling on it results in the uncoiling of the stent. The lead 125 is pulled until it is completely removed from the vessel thus providing the vessel 110 with several points of medial injury 130 induced by expansion of the stent 105 as shown in FIG. 20. To prevent collateral damage to the vessel, the lead 125 can be pulled throuqh a catheter or other guiding device (not shown) which straightens the wire of the stent 105 as it is withdrawn and prevents the wire from cutting into nearby vascular tissue as it is withdrawn. The result is removal of a long piece of relatively straight wire.

The coiled wire stent can thereby be removed at any time during the treatment protocol. Typically, the stent would be removed shortly after its expansion to induce media damage and before commencing an anti-restenosis treatment. If a very short duration of expanded stent induced damage is desired, it is possible to remove both the deflated balloon catheter and the coiled wire stent at the same time by grasping both simultaneously at their respective proximal ends and withdrawing from the body.

Conclusion

This porcine model for the proliferative component of human restenosis is accurate, simple, and develops in a short period of time. While this model may differ from human restenosis in its mechanism of production, the gross and histologic results appear identical to those found in human restenosis. Therapies aimed at reducing the occurrence of restenosis might thus be easily evaluated using this model.

While the invention has been described in connection with the preferred embodiments, it will be understood that it is not intended to limit the invention to those embodiments. On the contrary, it is intended to cover all alternatives, modifications, and equivalents, as may be included within the spirit and scope of the invention as defined by the appended claims.

We claim:

1. A method of modeling the treatment of proliferative human restenosis in a porcine blood vessel comprising the steps of:
   (a) introducing a balloon catheter having an expandable wire stent over the deflated balloon of the catheter into the lumen of the blood vessel of choice in a live pig and advancing the balloon to a selected location;
   (b) inflating the balloon to a pressure and a size sufficient to distort and fracture the internal elastic lamina of the blood vessel wall and force the wire stent through the elastic lamina into the media;
   (c) deflating and withdrawing the balloon catheter;
   (d) applying a selected anti-restenosis treatment to the pig; and
   (e) examining the selected location in the lumen of the treated pig for restenosis.

2. The method of claim 1 wherein the examination of the lumen for restenosis includes the steps of:
   (a) sectioning the blood vessel at the selected location;
   (b) measuring the degree of injury to the blood vessel in the section;
   (c) measuring the neointimal thickness in the section; and
   (d) comparing the neointimal thickness with the degree of injury.

3. The method of claim 1 wherein the stent wire is left in the blood vessel during the selected anti-restenosis treatment.

4. The method of claim 1 further comprising the step of removing the expanded stent wire prior to commencement of the selected anti-restenosis treatment.

5. The method of claim 4 wherein the stent wire is removed together with the balloon catheter.

* * * * *